(12) United States Patent
Pfenniger et al.

(10) Patent No.: US 7,241,413 B2
(45) Date of Patent: Jul. 10, 2007

(54) METHOD FOR PRODUCING A HOLLOW HANDLE FOR A TEETH CLEANING DEVICE

(75) Inventors: Philipp Pfenniger, Triengen (CH); Beat Huber, Buron (CH)

(73) Assignee: Trisa Holding AG, Triengen (CH)

( * ) Notice: Subject to any disclaimer, the term of this patent is extended or adjusted under 35 U.S.C. 154(b) by 623 days.

(21) Appl. No.: 10/181,709

(22) PCT Filed: Feb. 6, 2001

(86) PCT No.: PCT/CH01/00080

§ 371 (c)(1),
(2), (4) Date: Jul. 29, 2002

(87) PCT Pub. No.: WO01/58306

PCT Pub. Date: Aug. 16, 2001

(65) Prior Publication Data

US 2003/0037391 A1 Feb. 27, 2003

(30) Foreign Application Priority Data

Feb. 9, 2000 (DE) .................. 100 05 738

(51) Int. Cl.
*B29D 31/00* (2006.01)
*A46B 15/00* (2006.01)

(52) U.S. Cl. .................. 264/263; 264/243; 15/22.1; 15/143.1

(58) Field of Classification Search ............... 15/143.1, 15/22.1; 264/243, 263
See application file for complete search history.

(56) References Cited

U.S. PATENT DOCUMENTS

| 4,175,879 | A | * | 11/1979 | Molinari ............... 401/287 |
| 4,261,947 | A | * | 4/1981 | Ogi ............... 264/263 |
| 4,476,602 | A | * | 10/1984 | Hurn et al. ............... 15/28 |
| 4,544,588 | A |  | 10/1985 | Schauf |
| 4,799,280 | A | * | 1/1989 | Lee ............... 15/29 |
| 5,221,538 | A |  | 6/1993 | Gasami et al. |
| 5,707,166 | A | * | 1/1998 | Jeannet et al. ............... 403/24 |
| 5,718,014 | A | * | 2/1998 | deBlois et al. ............... 15/22.1 |
| 5,815,872 | A |  | 10/1998 | Meginniss, III et al. |
| 5,913,632 | A |  | 6/1999 | Persad |
| 5,934,762 | A |  | 8/1999 | Vrignaud |
| 6,319,448 | B1 | * | 11/2001 | Kirchdoerffer et al. ..... 264/263 |
| 2002/0120991 | A1 |  | 9/2002 | Cacka et al. |
| 2002/0124333 | A1 |  | 9/2002 | Hafliger et al. |

FOREIGN PATENT DOCUMENTS

| DE | 1904625 | 11/1964 |
| DE | 2024082 | 12/1971 |

(Continued)

*Primary Examiner*—Randall Chin
(74) *Attorney, Agent, or Firm*—Oliff & Berridge, PLC

(57) ABSTRACT

The invention relates to saucer-type handle components (5, 6) that pertain to a hollow handle and are produced in several steps. Said handle is used for a toothbrush. Said components are joined together and are inserted into an injection mould (25). A synthetic material, preferably a thermoplastic elastomer, is injection-moulded around the mould-parting line between the handle components (5, 6) in said injection mould (25). The connection seam (22) thus produced holds the two handle components (5, 6) together in a nondetachable manner and seals the hollow space (13) which is formed by the handle components (5, 6).

23 Claims, 6 Drawing Sheets

FOREIGN PATENT DOCUMENTS

| | | |
|---|---|---|
| DE | 2501291 A1 | 7/1976 |
| DE | 3312231 A1 | 10/1984 |
| DE | 4126041 | 2/1992 |
| DE | 42 41 409 C2 | 6/1994 |
| DE | 4417979 | 11/1995 |
| DE | 195 26 934 A 1 | 1/1997 |
| DE | 298 17 994.6 | 4/1999 |
| DE | 299 19 053 U 1 | 1/2001 |
| EP | 0683031 | 5/1995 |
| FR | 1 341 439 A | 1/1964 |
| FR | 2018293 | 5/1970 |
| GB | 1336613 | 11/1973 |
| WO | WO 00/21405 | 4/2000 |

* cited by examiner

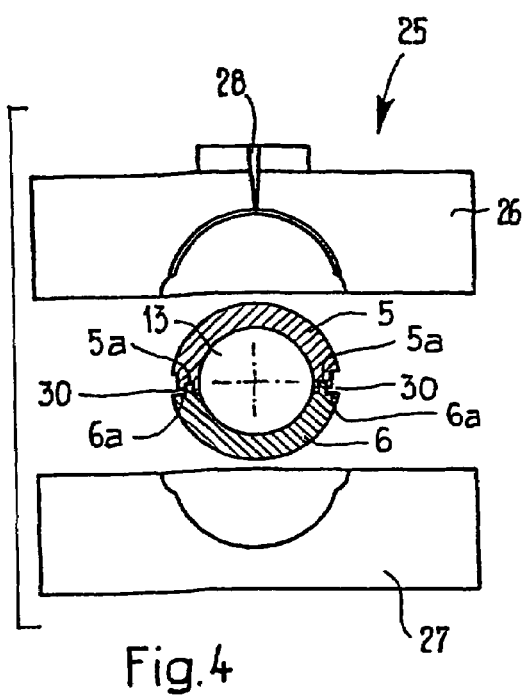 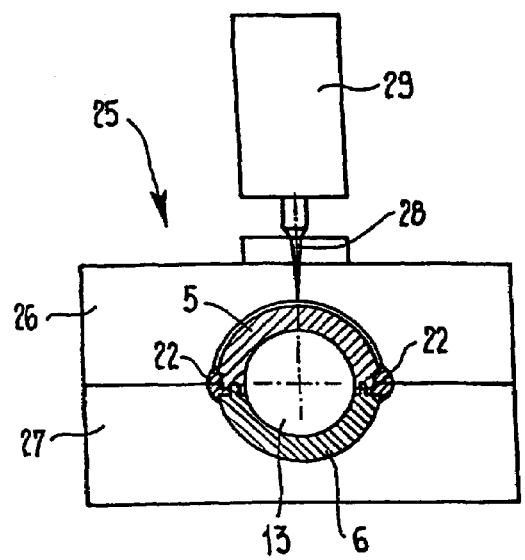
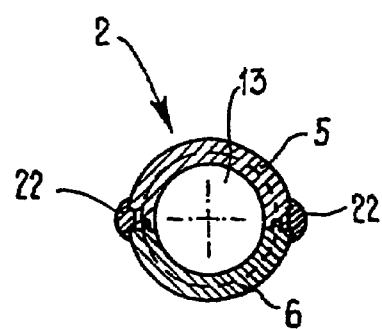

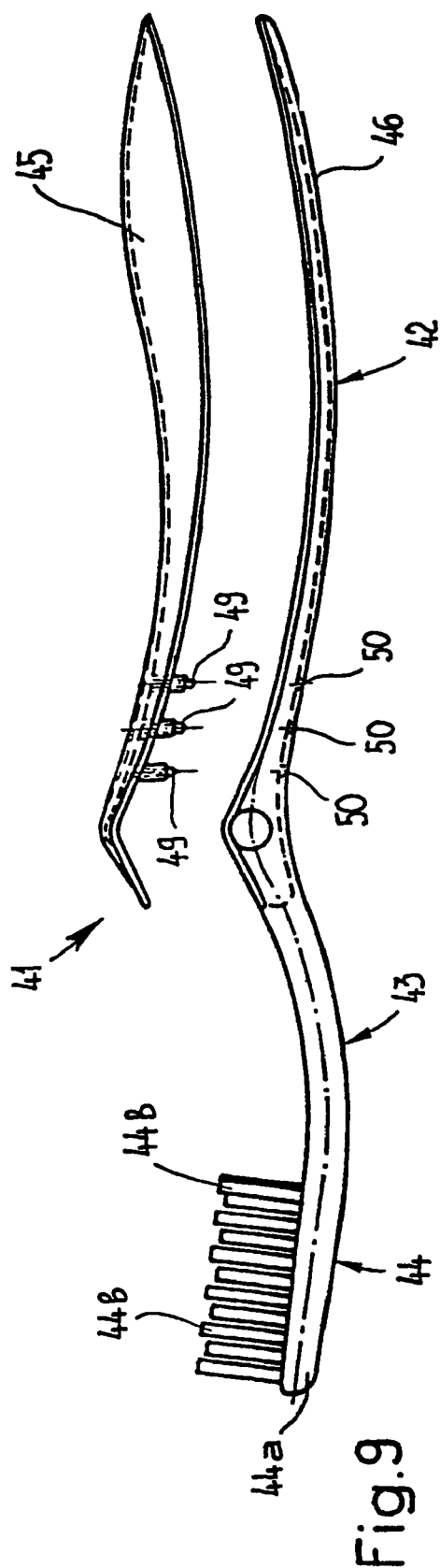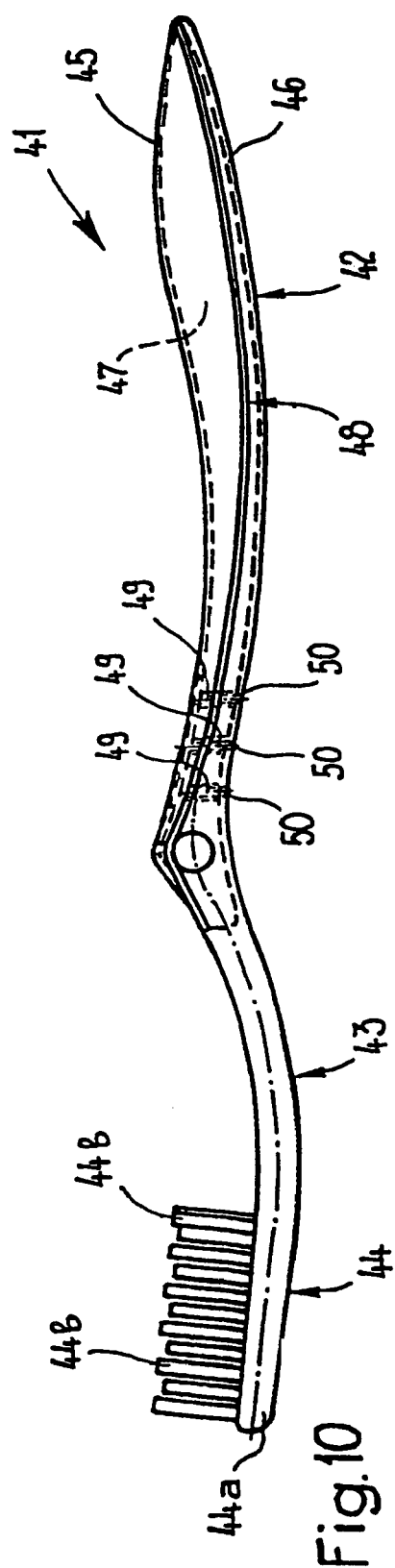
Fig.9
Fig.10

METHOD FOR PRODUCING A HOLLOW HANDLE FOR A TEETH CLEANING DEVICE

BACKGROUND

The present invention relates to a method for producing a hollow handle for a teeth cleaning device and to a handle produced by this method.

DE-U-298 17 994.6 discloses a toothbrush in which the hollow handle comprises two handle parts produced in separate steps, of which at least one handle part is formed in a shell-shaped manner. The two handle parts are welded to each other along the common parting join and are consequently connected to each other in a nondetachable manner. Adhesive bonding of the handle parts is also proposed.

A prerequisite for allowing handle parts consisting of plastic to be correctly welded to each other is that the handle parts consist of weldable plastics, i.e. plastics of the same family, which restricts the selection options for the plastics to be used.

SUMMARY

The present invention is consequently based on the object of providing a method of the type stated at the beginning that allows handle parts of a wide variety of materials to be joined together to form a hollow handle and connected to each other in an nondetachable and sealed manner.

The fact that, when the handle parts are joined together, they are coated or encapsulated with a plastics material along the common parting joint by the injection-molding process has the effect that a high-quality sealed connection, which can no longer be manually broken, is obtained between the handle parts.

BRIEF DESCRIPTION OF THE DRAWINGS

The subject matter of the invention is explained in more detail below on the basis of the drawings, in which purely schematically:

FIG. 6 shows a cross section through the handle comprising the two joined-together and interconnected handle parts, FIG. 9 shows in side view and in a representation corresponding to FIG. 1 another embodiment of a toothbrush before the handle parts are joined together, FIG. 10 shows in side view the toothbrush according to FIG. 8 in the assembled state.

DETAILED DESCRIPTION OF EMBODIMENTS

Figure 1:
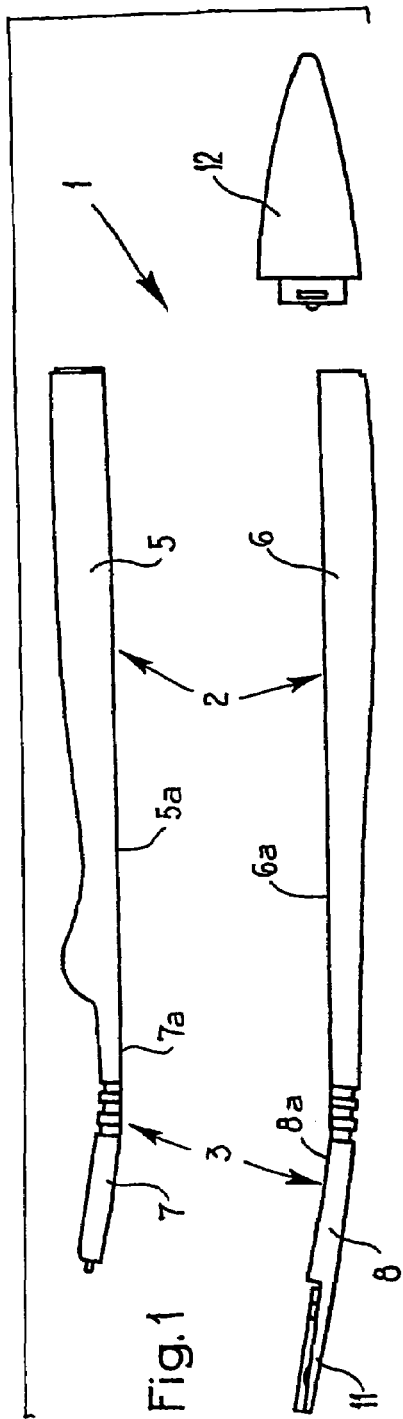
FIG. 1 shows in side view a toothbrush without the brush head, with the handle parts separate from each other.

A teeth cleaning device produced according to the invention, such as an electrically operated toothbrush 1, will be described on the basis of FIGS. 1–3.

The toothbrush 1 has a handle 2, which merges with a neck 3, to which a brush head 4 is attached. The handle 2 comprises two handle parts 5 and 6, of which at least the handle part 5 and preferably also the handle part 6 is formed in a shell-shaped manner. The neck 3 is formed by two neck parts 7, 8, which are formed in one piece with the assigned handle parts 5 and 6, respectively. The two neck parts 7a, 8a are likewise formed in a shell-shaped manner. The brush head 4 (FIG. 2) has a bristle carrier 9, from which clusters of bristles 10 protrude in a known way. The bristle carrier 9 is detachably mounted on a continuation 11 of the neck part 8. In the case of the present exemplary embodiment, the brush head 4 is consequently exchangeable. It goes without saying that it is also possible to form the bristle carrier 9 in one piece with the neck part 8, which in this case means that the brush head 4 is not exchangeable. Provided at the rear end of the handle 2 is a closure cap 12, which closes off a cavity 13 defined by the two shell-shaped handle parts 5 and 6. The closure cap 12 in the present exemplary embodiment is secured by means of a bayonet fastener. However, it is also possible, for example, for the closure cap 12 to be designed in such a way that it can be screwed on.

The hollow space 13 defined by the handle and neck parts 5, 6, 7, 8 is divided by a transverse wall 14, molded onto the handle part 5, into a rear hollow space 13a and a front hollow space 13b. In FIGS. 2, 15 denotes a detent groove which is provided on the inner side of the handle parts 5, 6 and belongs to the mentioned bayonet connection, by means of which the closure 12 is detachably secured to the handle 2. The rear hollow space 13a serves for receiving a battery (not represented), which is supported at one end on the closure cap 12 and at the other end on a contact spring 16, which is attached to the transverse wall 14. Accommodated in the neck 3 is a micro-motor 17, which is connected to a vibration element 18, for example an oscillating armature, which serves the purpose of making the brush head 4 vibrate. The micro-motor is connected to one terminal of the battery in the rear hollow space 13a by means of an electrical connecting line 19 via the closure cap 12. A further connecting line 20 connects the micro-motor 17 to a manually actuable switch 21, which is provided in the handle part 5 and is connected via a connecting line 20' to the contact spring 16, which is in contact with the other terminal of the battery. By actuating the switch 21, the micro-motor 17 is switched on and off. For securing or positioning the various electrical and mechanical parts of the drive for the brush head 4, positioning or holding parts, such as for example the transverse wall 14, are provided on at least one handle or neck part 5, 7 or 6, 8.

The handle 2 and the neck 3 preferably consist of the same material and either of the same plastic as the bristle carrier 9 or of a different kind of plastic. The handle and neck parts 5, 7 and 6, 8 are preferably produced by a one-component or multi-component injection-molding process.

Figure 2:
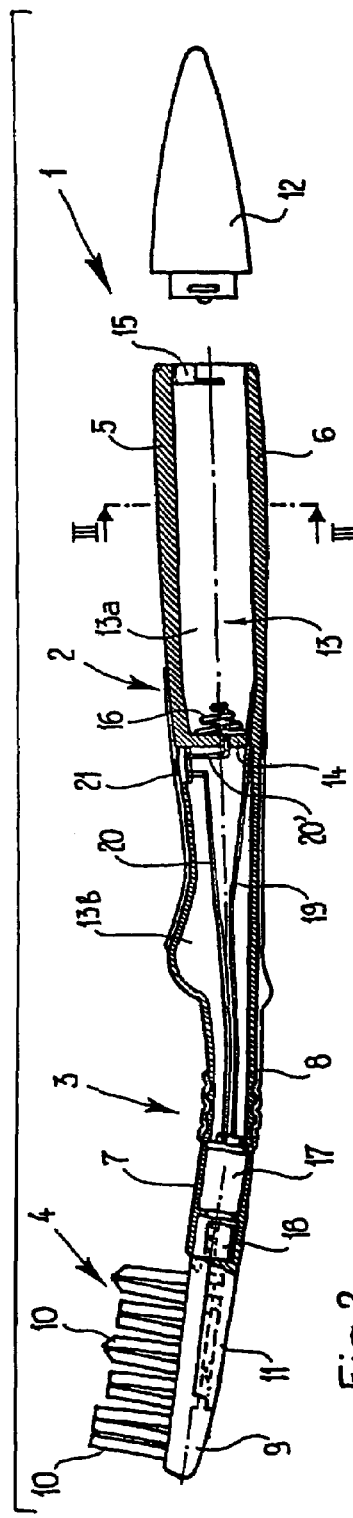
FIG. 2 shows in side view and partly in section the toothbrush put together from the two handle parts according to FIG. 1.

As FIGS. 1 and 2 reveal, the handle and neck parts 5, 7 and 6, 8 are produced in separate steps and then joined together. In this case, the end faces 5a, 7a and 6a, 8a of the parts 5, 7 and 6, 8 lying against one another form a parting joint therebetween, which is closed by means of a connection seam 22 (FIG. 3) in a way still to be described.

Figure 3:
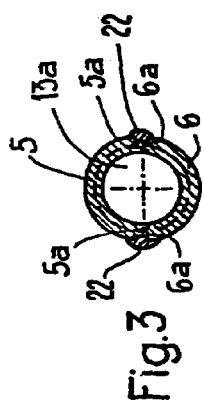
FIG. 3 shows a section along the line III—III in FIG. 2, FIGS. 4 and 5 show the injection mold for producing the connection seam between the handle parts.

The method for producing a toothbrush of the type shown in FIGS. 1–3 is now described on the basis of FIGS. 4–6.

The handle parts 5, 6 produced as mentioned in separate steps and for example at spatially separate locations, with molded-on neck parts 7 and 8, respectively, are joined together to form the finished handle 2 with neck 3. The handle parts 5, 6 joined together and possibly held together by additional mechanical means are then placed into an injection mold 25, such as that represented in FIG. 4. Of this injection mold 25, the two mold halves 26 and 27 are represented purely schematically. 28 denotes an injection opening provided in the upper mold half 26. The mutually facing end faces 5a and 6a and also the end faces 7a, 8a of the neck parts 7 and 8 define a parting joint 30. After the closing of the injection mold 25, i.e. the bringing together of the two mold halves 26, 27, a plastics material is injected by means of an only schematically represented injection unit 29 into the mold cavity of the injection mold 25 (FIG. 5). The injected plastics composition closes the parting joint 30 between the handle and neck parts 5, 6, 7 and 8 over its entire length or only over part of its length and then forms the connection seam 22. In FIG. 6, the finished handle 2, removed from the injection mold 25, is represented in cross section.

In the exemplary embodiment described, affinitive plastics are used for the handle and neck parts 5, 6, 7 and 8 and the connection seam 22, i.e. plastics which enter into a material bond with one another during the injection-molding operation. This is the case, for example, whenever polypropylene (PP) is used for the handle and neck parts 5, 6, 7, 8 and a corresponding thermoplastic material, preferably a thermoplastic elastomer, is used for the connection seam 22. Such a material bond is also obtained if the handle and neck parts 5, 6, 7, 8 consist of SAN (styrene acrylonitrile) and a corresponding thermoplastic material, for example a suitable thermoplastic elastomer, is used for forming the connection seam 22.

The method according to the invention, i.e. the closing of the parting joint 30 between the handle and neck parts 5, 6, 7, 8 by the injection-molding process has the advantage that even handle and neck parts which consist of plastics which are not affinitive with the plastic which is used for the connection seam 22 can be connected to one another in this way. This is the case, for example, if one handle or neck part 5, 7 consists of polypropylene (PP) and the other handle part 6, 8 consists of SAN and a thermoplastic elastomer that enters into a material bond either with PP or SAN and not with the other plastic is used for forming the connection seam 22. In such cases, no material bond is produced between the parts, requiring a different configuration of the connection seam and/or of the handle and neck parts. Such embodiments are now described on the basis of FIGS. 7 and 8, in which a handle 2' is shown in cross section.

Figure 7:
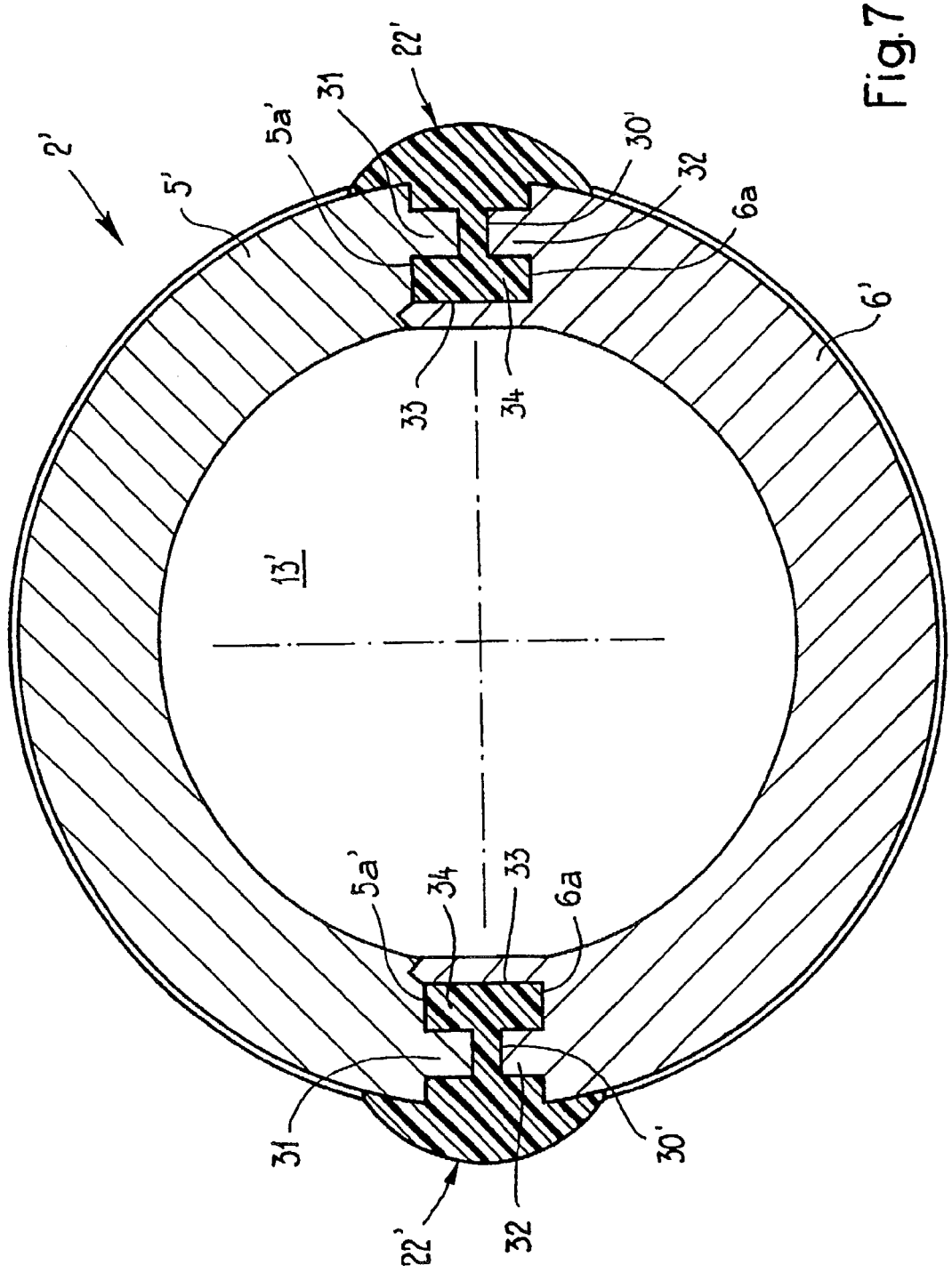
FIG. 7 shows in a representation corresponding to FIG. 6 but on an enlarged scale another form of the connection between the handle parts.

In the case of the embodiment shown in FIG. 7, in the mutually facing end faces 5a', 6a', defining the parting joint 30', there are preferably cleat-shaped projections 31, 32, which are surrounded by the plastics material of the connection seam 22'. The projections 31, 32 lying opposite one another form a hollow space 33, into which the injected plastics composition can penetrate. In FIG. 7, the part of the connection seam 22' lying in this space 33 is denoted by 34.

This formation provides a mechanical, i.e. positive and nonpositive, connection between the handle parts 5' and 6' and the connection seam 22'. It goes without saying that the positive or nonpositive connection between the handle parts 5', 6' and the connection seam 22' can also be produced in some other way, for example by providing depressions in the end faces 5a' and 6a' of the handle parts 5', 6', which are then filled with the plastics material of the connection seam 22'.

Figure 8:
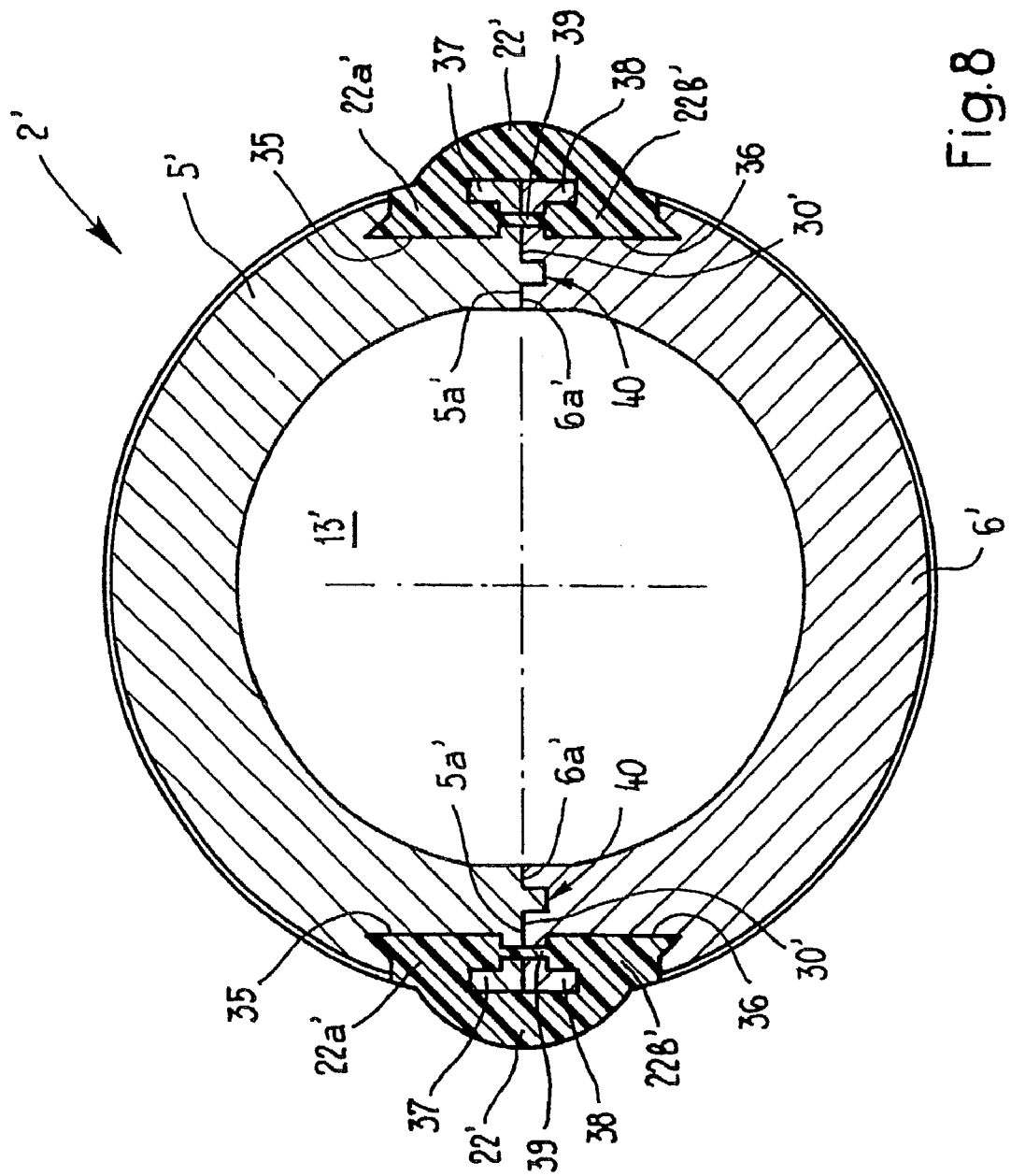
FIG. 8 shows in a representation corresponding to FIG. 7 a further form of the connection between the handle parts.

In the case of the exemplary embodiment according to FIG. 8, alongside the parting joint 30' in the two handle parts 5', 6' there are recesses 35 and 36, which are filled with the plastics material of the connection seam 22'. In this case, the parts 22a', 22b' of the connection seam 22' lying in these recesses 35, 36 grip behind cleat-like projections 37 and 38, respectively, of the handle parts 5', 6'. The recesses 35, 36 lying respectively opposite one another in the handle parts 5', 6' are respectively connected to one another over part of the length of the parting joint 30' by means of apertures 39, which are filled with the plastics material of the connection seam 22'. For holding together the joined-together handle parts 5', 6' before coating along the parting joint 30', in the region of the mutually facing end faces 5a', 6a' of the handle parts 5', 6' there are mechanical centering or holding arrangements 40, which in the exemplary embodiment according to FIG. 8 are formed in the manner of tongue-and-groove connections. Preferably associated with these tongue-and-groove connections are cleat-like projections in one handle part 5', which engage in equally and oppositely formed grooves in the other handle part 6'.

A mechanical connection of this type between the handle parts 5', 6' also makes it possible to produce one handle part or both handle parts from a material other than plastic, for example from a metal, such as for example nonferrous metal or aluminum, or even from wood.

The method explained on the basis of FIGS. 4–7 also allows toothbrushes designed differently than the toothbrush according to FIGS. 1–3 to be produced, as now explained by way of example with reference to FIGS. 9 and 10.

The toothbrush 41 shown in these FIGS. 9 and 10 comprises a handle 42, a neck 43 and a brush head 44. The latter has a bristle carrier 44a, which is in one piece with the neck 43 and is provided with clusters of bristles 44b. The handle 42 comprises an upper handle part 45, formed in a shell-shaped manner, and a lower handle part 46, which is in one piece with the neck 43 and may also be formed in a shell-shaped manner. The two handle parts 45, 46 define a hollow space 47. After the joining together of the two handle parts 45, 48, the parting joint is closed as already described by means of a plastics material in the injection-molding process. The connection seam formed thereby is denoted by 48 (FIG. 9).

The two handle parts 45, 46 are positioned with respect to each other and held together by mechanical means before the coating of the parting join with the plastics material. For this purpose, the upper handle part 45 is provided with downwardly protruding, pin-like lugs 49, which engage in openings 50 provided in the lower handle part 46 when the handle parts 45, 46 are joined together.

The two handle parts 45, 46 are produced in separate steps. If the handle parts 45, 46 consist of plastic, they are preferably produced by the one-component or multi-component injection-molding process.

After the joining together of the handle parts 45, 46, the handle 42 is coated by a plastics material in an injection mold in the region of the parting joint between the handle parts 45, 46, as has been explained on the basis of FIGS. 4–6.

In the case of the exemplary embodiments described above, the handle parts 5, 6, 45, 46 are produced in separate locations from one another, preferably by the injection-molding process, are subsequently joined together and are then encapsulated along the parting joint 30 with the plastics material of the connection seam 22, 48 in a further injection-molding operation.

It is also conceivable, however, to perform certain steps among these at the same location. For example, firstly a first handle part may be produced. A second handle part is produced in a two-component injection mold and remains in this injection mold. The first handle part is joined together with the second handle part in the injection mold, for example with the aid of a robot. Then the forming of the connection seam takes place in this two-component injection mold, possibly after the joined-together handle parts have been transferred into a further cavity of the injection mold, for example by means of a robot, by injecting the corresponding plastics material. It is also possible to bring the second handle part into the further cavity, then join the first handle part together with the second handle part, and after that form the connection seam by injecting the corresponding plastics material into this further cavity.

Figure 11:
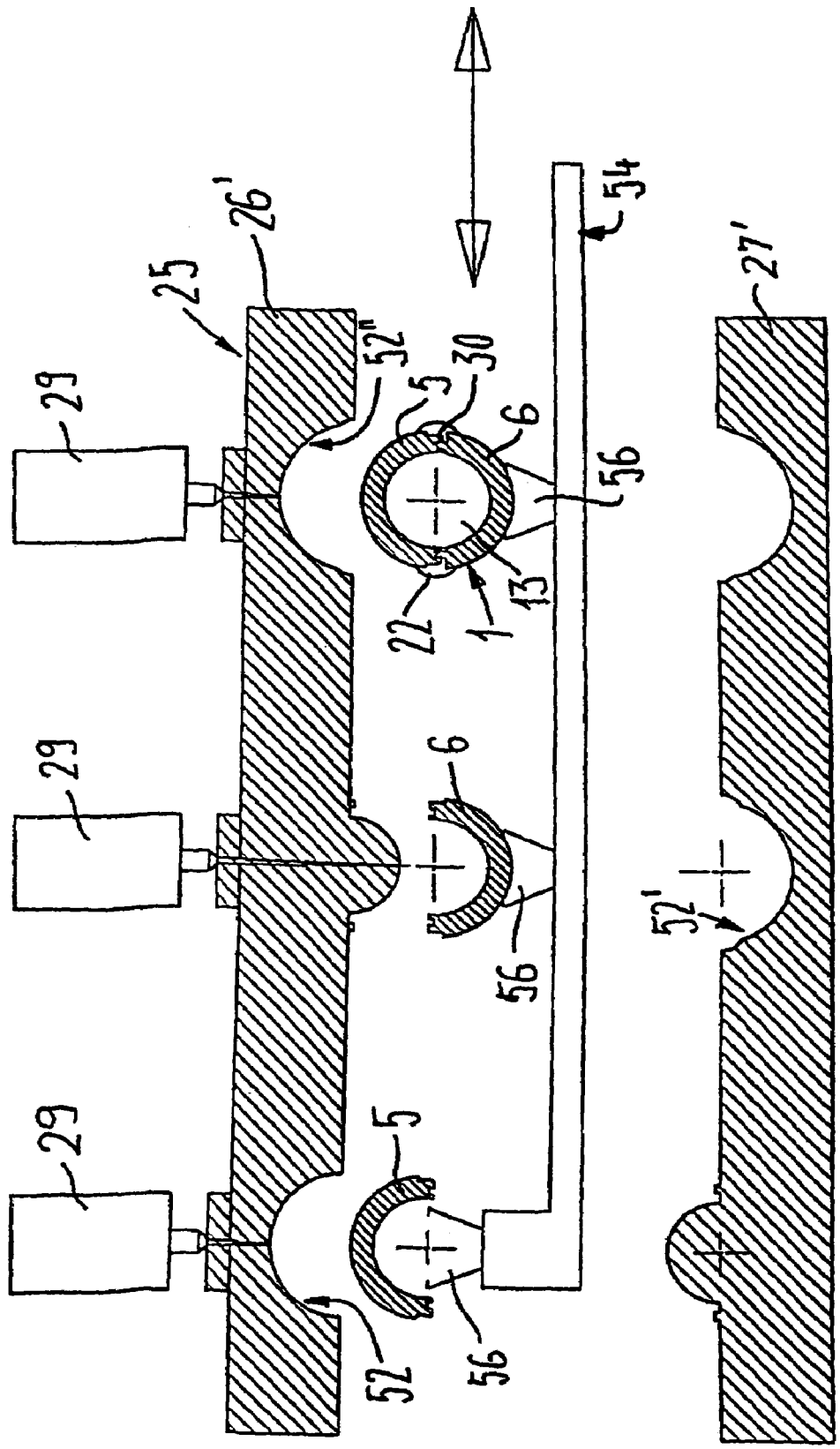
FIG. 11 shows the injection mold for producing the handle parts and the connection seam.

The production of the two handle parts and of the connection seam may also take place at the same location, i.e. in a multi-component injection-molding installation, which is explained on the basis of FIG. 11.

FIG. 11 shows in the same representation as FIGS. 4 and 5 the two mold halves 26' and 27' of a three-component injection mold 25'. In a first cavity 52, the first handle part 5 is produced—with the injection mold 25' closed—by injecting the corresponding plastics material by means of the assigned injection unit 29. At the same time, in a second cavity 52' of the injection mold 25', the second handle part 6 is produced by injecting another plastics material by means of the assigned injection unit 29. Finally, likewise at the same time, in a third cavity 52" of the injection mold 25', the connection seam 22 is formed between the handle parts 5 and 6, produced in a preceding injection cycle and then joined together, by injecting a further different plastics material by means of the assigned injection unit 29.

54 denotes a robot arm, having suction heads 56 for the handle parts 5, 6 and the toothbrush 1. With the mold halves 26', 27' separated from each other after an injection operation, the suction heads 56, which can be connected to a vacuum source, simultaneously grasp the two handle parts 5, 6 and the toothbrush 1 and lift them out of the corresponding cavities 52, 52', 52".

The first handle part 5 is then inserted by means of the robot arm 54 into the third cavity 52" of the mold half 26' and released by deactivating the corresponding suction head 56. Subsequently, the handle parts 5, 6 are joined together, in that the robot arm 54 places the second handle part 6 onto the first handle part 5. By deactivating the assigned suction head 56, the second handle part 6 is released. Once the robot arm 54 has been moved out of the region of the injection mold 25'—also for discharging the toothbrush 1—, the two mold halves 26', 27' are moved toward each other, in order to close the injection mold 25' for the next injection operation.

It is also possible to join the two handle parts 5, 6 together outside the injection mold 25'—for example during an injection operation—and then place them in the third cavity 52". This procedure is advantageous in particular when further parts are to be introduced into the cavity 13 or one of the handle parts 5, 6 is to be provided with a surface finish or be printed on.

It should be mentioned for the sake of completeness that it is of course also possible to feed more than one of the cavities 52, 52', 52" by means of a common injection unit 29. This is so if the handle parts 5, 6 consist of the same plastics material, or the plastics material for the connection seam 22 is also used for producing a membrane on one or both handle parts 5, 6.

It goes without saying that the injection mold 25' may have a number of rows of first, second and third cavities 52, 52', 52" for the simultaneous production of a number of toothbrushes 1.

As described, preferably a soft plastic, i.e. a plastic that remains elastomeric, with a Shore hardness of preferably 10–70, is used for the forming of the connection seam 22, 48. However, it is also possible to use a hard plastic in the same way as for the handle and neck parts.

At least the upper handle part 5 or 44 may be opaque entirely or in certain regions or transparent entirely or in certain parts.

The hollow space 13, 47 in the handle 2, 42 may be filled with a liquid and/or items. In the case of toothbrushes, as they are shown in FIGS. 8 and 9, the filling of the hollow space takes place before the injection-molding of the connection seam.

The fact that the connection seam 22, 48 consists of plastic allows the connection seam also to be used as an element in the visual design, by choosing the color of the plastic.

In the same injection-molding operation in which the plastics material for the connection seam is injected, other regions of the handle, of the neck or of the brush head, for example the finger resting region or sealing elements, may also be formed from this plastics material.

The invention claimed is:

1. A method for producing a hollow handle for a personal hygiene device, comprising:
    forming at least two handle parts, at least one of the handle parts being formed in a shell-shaped manner;
    forming on one of the handle parts protruding pin-like lugs and on the other handle part corresponding openings, the lugs and the openings forming inter-engaging holding means;
    joining the at least two handle parts together so that mutually opposed end faces of the at least two handle parts define a common parting joint therebetween;
    mechanically holding the joined-together handle parts in a predetermined relative position by the inter-engaging holding means formed on the handle parts;
    introducing the joined-together handle parts into an injection mold; and
    filling the common parting joint between the joined-together handle parts in an injection molding operation with a thermoplastic elastomer to secure the at least two handle parts together and form a connection seam, wherein the inter-engaging holding means are provided in a region remote from the connection seam at the parting joint.

2. The method as claimed in claim 1, further comprising forming other regions of the handle from the thermoplastic material with which the parting joint is filled.

3. The method as claimed in claim 2, further comprising forming finger rest regions, sealing elements, or membranes on the handle from the thermoplastic material with which the parting joint is filled.

4. The method as claimed in claim 2, wherein the filling of the parting joint and the formation of the other regions of the handle take place during the same injection-molding operation.

5. The method as claimed in claim 2, wherein the thermoplastic material for forming the other regions of the handle is injected from a same injection unit as the thermoplastic material for filling the parting joint.

6. The method as claimed in claim 1, wherein, before the parting joint is filled, items and/or liquid are introduced into the at least one shell-shaped handle part.

7. The method as claimed in claim 6, wherein the items include electrical components of the device.

8. The method as claimed in claim 1, wherein the handle parts are made from plastic.

9. The method as claimed in claim 1, wherein at least one handle part is made from a transparent plastic.

10. The method as claimed in claim 1, wherein said thermoplastic material has a Shore hardness of 10–70.

11. The method as claimed in claim 1, wherein at least one of the handle parts is provided with recesses, which are filled with the thermoplastic material during filling of the parting joint.

12. The method as claimed in claim 1, further comprising forming a hollow interior space by the joined-together handle parts.

13. The method as claimed in claim 1, wherein at least one of the two handle parts comprises a plastic that enters into a material bond with the thermoplastic material of the parting joint.

14. The method as claimed in claim 1, wherein at least two of the handle parts comprise plastics that enter into a material bond with the thermoplastic material of the parting joint.

15. The method as claimed in claim 1, wherein one of the handle parts is formed of a material other than plastic.

16. The method as claimed in claim 1, further comprising providing at least two of the handle parts with passages that are flush with one another in the joined-together state and filled with the thermoplastic material during the filling of the parting joint.

17. The method as claimed in claim 1, wherein the handle parts are produced with different shapes.

18. The method as claimed in claim 1, wherein an upper handle part is made at least partially from a transparent plastic.

19. The method as claimed in claim 1, wherein one of the at least two handle parts is provided with a surface finish or printed on before the handle parts are introduced into the injection mold.

20. The method as claimed in claim 19, wherein at least the handle part provided with a surface finish or printed on is made from a transparent plastic.

21. The method as claimed in claim 1, wherein the personal hygiene device is a toothbrush.

22. A method for producing a hollow handle for a personal hygiene device, comprising:

forming at least two handle parts from plastic in separate steps, at least one of the handle parts being formed in a shell-shaped manner and at least one of the handle parts being made of a transparent material;

forming on one of the handle parts protruding pin-like lugs and on the other handle part corresponding openings, the lugs and the openings forming inter-engaging holding means;

joining the at least two handle parts together so that mutually opposed end faces of the at least two handle parts define a common parting joint therebetween;

mechanically holding the joined-together handle parts in a predetermined position by the inter-engaging holding means;

introducing the joined-together handle parts into an injection mold; and forming a connection seam by filling the common parting joint between the joined-together handle parts in an injection molding operation with a thermoplastic elastomer to secure the at least two handle parts together, at least one of the handle parts being formed of a plastic material that enters into a material bond with the thermoplastic elastomer forming the connection seam and at least one of the handle parts being formed of a plastic material that does not enter into a material bond with the thermoplastic elastomer.

23. A method as claimed in claim 22, wherein the personal hygiene device is a toothbrush.

* * * * *